United States Patent
Snijder et al.

(10) Patent No.: US 10,076,588 B2
(45) Date of Patent: Sep. 18, 2018

(54) SURGICAL REPAIR PRODUCT COMPRISING UHMWPE FILAMENTS

(75) Inventors: Carina S Snijder, Sittard (NL); Rogier Oosterom, Maastricht (NL); Christiaan H. P. Dirks, Dilsen (BE)

(73) Assignee: DSM IP ASSETS B.V., Heerlen (NL)

( * ) Notice: Subject to any disclaimer, the term of this patent is extended or adjusted under 35 U.S.C. 154(b) by 1529 days.

(21) Appl. No.: 12/097,346

(22) PCT Filed: Nov. 28, 2006

(86) PCT No.: PCT/EP2006/011405
§ 371 (c)(1),
(2), (4) Date: Oct. 31, 2008

(87) PCT Pub. No.: WO2007/071309
PCT Pub. Date: Jun. 28, 2007

(65) Prior Publication Data
US 2009/0306709 A1    Dec. 10, 2009

Related U.S. Application Data

(60) Provisional application No. 60/752,601, filed on Dec. 22, 2005.

(30) Foreign Application Priority Data

Dec. 22, 2005 (EP) .................................. 05078012

(51) Int. Cl.
| A61B 17/04 | (2006.01) |
| A61L 17/04 | (2006.01) |
| A61L 31/04 | (2006.01) |
| C08L 23/06 | (2006.01) |

(52) U.S. Cl.
CPC .............. *A61L 17/04* (2013.01); *A61L 31/04* (2013.01); *C08L 23/06* (2013.01)

(58) Field of Classification Search
CPC ............ A61B 17/04; D10B 2321/0211; D10B 2401/062; D10B 2509/00

USPC .......................................... 428/364; 606/228
See application file for complete search history.

(56) References Cited

U.S. PATENT DOCUMENTS

| 4,375,957 A | * | 3/1983 | Smith ............................. 432/2 |
| 2003/0050667 A1 | * | 3/2003 | Grafton et al. ............... 606/228 |
| 2005/0149119 A1 | * | 7/2005 | Koyfman et al. ............. 606/228 |

FOREIGN PATENT DOCUMENTS

| EP | 1 293 218 | 3/2003 |
| EP | 1 543 782 | 6/2005 |
| GB | 2 042 414 | 9/1980 |
| WO | 2005/066401 | 7/2005 |
| WO | 2006/010522 | 2/2006 |

OTHER PUBLICATIONS

International Search Report for PCT/EP2006/011405 dated Jun. 1, 2007.
Written Opinion for PCT/EP2006/011405 dated Jun. 1, 2007.
Wang et al., "New approach for processing ultrahigh-molecular weight polyethylene powder. Solid-state rolling followed by hot stretch (roll-draw)", *Journal of Polymer Science, Part B: Polymer Physics*, vol. 28, No. 12, Nov. 1990, pp. 2441-2444, XP002384573.

* cited by examiner

*Primary Examiner* — Andrew Piziali
(74) *Attorney, Agent, or Firm* — Nixon & Vanderhye P.C.

(57) ABSTRACT

The invention relates to an elongate surgical repair product comprising a cable of which bending stiffness can be lowered, which fibrous member is a heat-set cable comprising at least 50 mass % of high-performance polyethylene yarn. The product shows very high tenacity, combined with a relatively high initial bending stiffness that is significantly reduced upon bending or flexing the member, without significant dimensional change; and allows both easy and well-controlled handling and good knot tying characteristics. The invention also relates to a method of making said elongate product.

12 Claims, No Drawings

SURGICAL REPAIR PRODUCT COMPRISING UHMWPE FILAMENTS

This application is the U.S. national phase of International Application No. PCT/EP2006/011405 filed 28 Nov. 2006 which designated the U.S. and claims priority to European Patent Application No. 05078012.1 filed 22 Dec. 2005 and U.S. Provisional Application No. 60/752,601 filed 22 Dec. 2005, the entire contents of each of which are hereby incorporated by reference.

The invention relates to an elongate surgical repair product comprising a cable of which bending stiffness can be lowered. The invention also relates to a method of making said surgical repair product and said cable.

Such a surgical repair product is known from U.S. Pat. No. 4,510,934. An elongate surgical repair product is understood to be an article for use as for example a surgical suture for approximating soft body tissue, or as a cable, tape, ribbon or band for fixing or retaining body parts like bones, or as artificial ligament or tendon. Elongate means the product is of length dimension much larger than its cross-sectional dimensions (width, thickness). The repair product comprises at least one elongate fibrous member that typically functions as load-bearing component, which member contains strands comprising biocompatible fibres. The repair product may further comprise for example a bone anchor, a needle, a coating material, etc. Strands are the structural elements forming the member, and may contain one or more monofilaments and/or multifilament yarns. A multifilament yarn is a bundle of a plurality of continuous filaments, which may have been given a certain twist level to provide the yarn with some coherency.

Elongate surgical repair products like sutures have been made over time from a variety of materials for forming the strands, including flax, hair, cotton, silk, animal gut, and synthetic materials like polyesters, polyamides, and polyolefins like polyethylene or polypropylene. The material used may be absorbable or non-absorbable. Non-absorbable products are not dissolved or degraded by the body's natural action after implantation. Relevant material properties for use in sutures and other repair products include tensile strength, flexibility, elasticity, wettability, and other surface properties. A relatively new material for making a non-absorbable surgical repair product, is multi-filament yarn made from ultra-high molar mass polyethylene (UHMWPE). The main advantages of this material include its biocompatibility, its good abrasion resistance, its flexibility, and especially its very high tensile strength. High-performance (or high-strength) polyethylene (HPPE) yarn is herein understood to be a multifilament polyethylene yarn having a tensile strength of more than 2.0 N/tex. Such yarn is called biocompatible if it fulfils the relevant requirements, of for example the FDA, with regard to other components being present in addition to the UHMWPE polymer (such as processing additives, spin finish, solvent residues, and the like).

Elongate surgical repair products like sutures generally contain a braided structure made from multifilament yarn as fibrous member. Such braided structure provides a combination of good strength properties (of course dependent on the type of filaments contained therein) and high bending flexibility, enabling easy forming and securing of knots to fixate the product. A disadvantage of its high flexibility, or low bending or flexural stiffness, is that the product is more difficult to handle by a surgeon, for example in threading through the eye of a surgical needle or inserting in a wound, than e.g. animal gut or monofilament-based sutures.

This problem was also addressed in U.S. Pat. No. 4,510,934. The surgical product described therein is indicated to be stiff during a sewing operation, but flexible and easily knotted during the tying procedure: the elongate surgical repair product comprises a fibrous member of bending stiffness that can be lowered during a surgical operation, which member consists of a monofilament core and a braided flexible sheath surrounding said core; the core acting as a stiffener for the sheath, and the core and sheath being separably fastened together. The member consisting of said combination of core and sheath is initially used by the surgeon for threading (through a needle's eye and/or through a patient's tissue), and once at the desired location the monofilament core is separated and removed from the braided sheath, such that the tying and securing of a knot is done solely with the flexible braided part (having lower bending stiffness than the initial member containing the monofilament core).

A disadvantage of the surgical repair product known from U.S. Pat. No. 4,510,934 is that the core has to be removed during the surgical procedure in an additional, cumbersome handling step. Such removal subsequently results in a product of smaller dimensions; or otherwise stated, a thicker than necessary surgical repair product has to be used in the surgical procedure, leading to more than needed damage to tissue and the like. In addition, handling properties dramatically change upon removing the core; including for example lengthening of the remaining braided part.

There is thus a need for a surgical repair product such as a suture, which has excellent strength properties, and flexural stiffness characteristics that allow easy handling and good control during threading or sewing operations, as well as effective forming and securing of surgical knots, but which does not show said disadvantages.

The object of the invention is therefore to provide an elongate surgical repair product of high strength, and of which bending stiffness can be reduced without having to remove a component from the product, or significantly altering its dimensions.

This object is achieved according to the invention with an elongate surgical repair product wherein the fibrous member is a heat-set cable comprising at least 50 mass % of high-performance polyethylene yarn.

The elongate surgical repair product according to the invention shows very high tenacity, combined with a relatively high initial bending stiffness that is significantly reduced upon simply bending or flexing the member, without having to remove a component or significant dimensional changes; thus allowing both easy and well-controlled handling and showing good knot tying characteristics. The product according to the invention can be handled by a surgeon using his existing auxiliary instruments, designed for relatively stiff repair products. Such properties are especially advantageous in minimal invasive surgical procedures. A further advantage of the product according to the invention is that also after implanting in a patient's body, the product becomes more flexible as a result of movements, and causes less irritation. A further advantage is that the fibrous member shows little stress relaxation in tensioned conditions, e.g. requiring less adjustment after being applied, and enabling more constant long-term fixation of bone parts by an orthopedic cable (as for example in sternotomy repair or bone fracture fixation). The fibrous member further has a smooth surface without protruding filaments, and a low surface area related to its volume, e.g. decreasing the risk of infections caused by micro-organism entrapped in the member.

An elongate surgical repair product wherein the fibrous member is a cable comprising high-performance polyethylene yarn may be known from other publications, like EP 0561108 A2, EP 12933218 A1, and EP 1543782 A1, but these publications are silent on such product having increased bending stiffness resulting from a heat-treatment, let alone that such stiffness can be reduced again upon bending or flexing. In EP 1543782 A1 a suture containing 38 mass % of HPPE yarn and 62 mass % of bio-absorbable polydioxanone yarn is disclosed, which suture is indicated to have been post-stretched at 90° C. This suture is stated to have better, that is lower bending stiffness than a commercial suture made from HPPE and PET yarns.

The invention relates to an elongate surgical repair product comprising a fibrous member comprising high-performance polyethylene (HPPE) yarn.

HPPE yarn is understood to be a multi-filament yarn of a plurality of ultrahigh molar mass polyethylene filaments, which can be made from UHMWPE polymer by a process generally referred to as gel spinning. Gel spinning of ultra-high molecular weight polyethylene (UHMWPE) is well known to the person skilled in the art; and described in numerous publications, including EP 0205960 A, EP 0213208 A1, U.S. Pat. No. 4,413,110, GB 2042414 A, EP 0200547 B1, EP 0472114 B1, WO 01/73173 A1, and Advanced Fiber Spinning Technology, Ed. T. Nakajima, Woodhead Publ. Ltd (1994), ISBN 1855-73182-7, and references cited therein. Gel spinning is understood to include at least the steps of spinning at least one filament from a solution of ultra-high molecular weight polyethylene in a spin solvent; cooling the filament obtained to form a gel filament; removing at least partly the spin solvent from the gel filament; and drawing the filament in at least one drawing step before, during or after removing spin solvent. Suitable spin solvents include for example paraffins, mineral oil, kerosene or decalin. Spin solvent can be removed by evaporation, by extraction, or by a combination of evaporation and extraction routes. Such HPPE yarns are commercially available as Spectral® or Dyneema® grades.

The HPPE yarn of a plurality of ultra-high molar mass polyethylene filaments indicates that in addition to filaments there may be small amounts, e.g. at most 5 mass %, of other components present, like a coating or sizing. Preferably, the HPPE yarn contains at most 1 mass % of biocompatible other components.

Within the context of the present application UHMWPE is understood to be polyethylene with an intrinsic viscosity (IV, as determined according to method PTC-179 (Hercules Inc. Rev. Apr. 29, 1982) at 135° C. in decalin, with dissolution time of 16 hours, with anti-oxidant DBPC in an amount of 2 g/l solution, and the viscosity at different concentrations extrapolated to zero concentration) of above 5 dl/g. Particularly suitable is UHMWPE with IV of between about 8 and 40 dl/g, more preferably between 10 and 30, or 12 and 28, or between 15 and 25 dl/g. These ranges represent an optimum in polymer processability and filaments properties. Intrinsic viscosity is a measure for molar mass (also called molecular weight) that can more easily be determined than actual molar mass parameters like $M_n$ and $M_w$. There are several empirical relations between IV and $M_w$, but such relation is highly dependent on molar mass distribution. Based on the equation $M_w=5.37\times10^4 [IV]^{1.37}$ (see EP 0504954 A1) an IV of 8 dl/g would be equivalent to Mw of about 930 kg/mol.

Preferably, the UHMWPE is a linear polyethylene with less than one branch or side chain per 100 carbon atoms, and preferably less than one side chain per 300 carbon atoms, a branch usually containing at least 10 carbon atoms. The linear polyethylene may further contain up to 5 mol % of one or more comonomers, such as alkenes like propylene, butene, pentene, 4-methylpentene or octene.

In a preferred embodiment, the UHMWPE contains a small amount of relatively small groups as side chains, preferably a C1-C4 alkyl group. It is found that a filament from UHMWPE with a certain amount of such groups show reduced creep behaviour. Too large a side chain, or too high an amount of side chains, however, negatively affects the processing and especially the drawing behaviour of the filaments. For this reason, the UHMWPE preferably contains methyl or ethyl side chains, more preferably methyl side chains. The UHMWPE therefore contains preferably at least 0.2, 0.3, 0.4 or 0.5 methyl or ethyl side chains. The amount of side chains is preferably at most 20, more preferably at most 10 per 1000 carbon atoms.

The UHMWPE can be a single polymer grade, but also a mixture of two or more different grades, e.g. differing in IV or molar mass distribution, and/or number of side chains.

The UHMWPE filaments may further contain usual amounts, generally less than 5 mass % of customary additives, such as anti-oxidants, thermal stabilizers, colorants, nucleating agents, flow promoters, catalyst residues etc.; as long as these components are suitable for the use in a surgical product. The UHMWPE filaments preferably contain less than 800 ppm of residual amounts of spin solvent, more preferably less than 500, 250, or even less than 100 ppm. The filaments may also contain other polymers, preferably polyolefinic polymers, like other polyethylenes, polypropylenes, or their copolymers, including rubbery copolymers like EPDM, EPR, etc. The amount of such other polymer is always lower than the amount of UHMWPE in the filament, and is preferably not more than 30 mass %, or more preferably not more than 20, 10 or 5 mass % of the UHMWPE filament.

The elongate surgical repair product according to the invention comprises a cable comprising high-performance polyethylene yarn, which cable can be of various constructions, generally made up from a plurality of strands. Suitable examples include knitted structures, wovens, various braided constructions, or combinations thereof. Preferably, the cable is of a braided construction comprising at least 3 strands, which combines strength and flexibility. A braided cable is in fact the construction generally used for making surgical repair products. Suitable braided cables include (hollow or solid) tubular or circular braids, spiroid braids, or flat braids if an oblong cross-section is preferred rather than a round member. It is also possible to apply a so-called core-sheath (sometimes called kern-mantle) braid, or a braid-on-braid construction as the cable, especially for heavier cables of larger diameter. In a core-sheath braid there is a core that is formed from mainly parallel filaments or twisted yarns surrounded by a braided cover or sheath, whereas a braid-on-braid has a braided core and braided sheath.

The cable may contain a plurality of strands of various constructions. Suitable examples of a strand include parallel filaments or a single multifilament yarn, two or more twisted (or otherwise assembled) yarns, but also knitted or braided constructions, or combinations thereof. Preferably, the strand is a single yarn, or two or more yarns twisted together.

The cable may in addition to the strands further comprise other components, for example compounds that provide some functional effect, like anti microbial or anti-inflammatory action, or that further improve knotting performance.

The amount of such other components is generally limited to at most 20 mass % (relative to total cable mass), preferably at most 10, or at most 5 mass %.

The elongate surgical repair product according to the invention comprises a cable that comprises at least 50 mass % of high-performance polyethylene yarn. The HPPE yarns are the components that contribute most to the strength properties of the cable (or fibrous member), which is the load-bearing component of the product according to the invention. In addition, the HPPE yarns provide the bending stiffness behaviour of the heat-set cable. For this reason, the cable preferably comprises at least 60 mass % of HPPE yarn (relative to total mass of the cable); more preferably at least 70, 80 or at least 90 mass %. The cable may further comprise other fibrous materials, e.g. other biocompatible materials like polymers, to provide some other additional properties to the member, including improved knot slip behaviour or visual contrast. Fibrous material is herein understood to mean fibres of relatively low diameter, preferably of size below 20 dtex; such as a multifilament yarn or a spun yarn based on staple fibres. Such other fibres are generally present in the form of one or more strands in the cable. The cable may contain at least 25 mass % of other fibrous material, preferably at least 20, 15, or 5 mass %, to arrive at a certain combination of properties. If the cable is a core-sheath braid or a braid-on-braid construction, the amount of HPPE fibres in the core and sheath can be the same, but also different. A high HPPE content of the core is advantageous for a high tenacity of the cable, whereas a high HPPE content in the sheath results in a heat-set cable with relatively high initial bending stiffness, which can be substantially lowered upon bending.

In a special embodiment, the surgical repair product according to the invention comprises a braided cable of core-sheath structure, wherein the core consists substantially of HPPE yarns for optimum strength performance, and the sheath contains HPPE yarn in combination with a polyester yarn. In another preferred embodiment, the product according to the invention comprises a braided cable of core-sheath structure, wherein the sheath consists substantially of HPPE yarns.

Suitable examples of other fibrous materials include filaments or staple fibres made from non-absorbable polymers like other polyolefins, fluoro-polymers, or semi-aromatic polyesters like polyethylene terephthalate, absorbable polymers like aliphatic polyesters based on e.g. lactides, but also small metal fibres or particles for X-ray visibility The HPPE yarn in the product according to the invention has a tenacity of at least 2.0 N/tex; preferably its tenacity is at least 2.5, 2.8, or even at least 3.1 N/tex for optimum strength properties of the product. Maximum strength of UHMWPE fibres, as predicted by different theories, is not yet reached by available yarns; in practice the upper limit for tenacity may currently be on the order of 5 or 6 N/tex.

The cable of the elongate surgical repair product according to the invention may contain strands that have a titer (or linear density) that may vary widely, for example from 5 to 3000 dtex. For making thicker or heavier members preferably more strands are used, rather than thicker strands, to better control flexibility of the construction. Preferably, the strand in the member according to the invention has a titer of at least 15 dtex, more preferably at least 25, 50, 100, 200, or at least 300 dtex. The strand titer is preferably at most about 2750, 2500, 2250, 2000, 1800 dtex or even at most 1600 dtex to result in a more flexible member.

The yarn in the strand preferably has a titer range as indicated above if the strand contains only one yarn; preferred titer ranges for other cases can be calculated analogously.

The size of the member (cable) in the product according to the invention can be in the full USP range for sutures (e.g. 1210 to 10), but is not limited thereto. For application as for example orthopedic cables, artificial tendon or ligament a member can have a (round) cross-section of up to about 5 mm. Expressed otherwise, suitable members can have a linear density or titer that varies in a wide range, for example from 2 to 20000 tex, preferably about 20-3000 tex.

The elongate surgical repair product according to the invention comprises a heat-set cable of which bending stiffness can be lowered. Within the context of the present invention a heat-set cable is understood to be a cable comprising at least 50 mass % of high-performance polyethylene yarn that substantially consists of a plurality of UHMWPE filaments, which cable has been subjected to a heat treatment at elevated temperature, but below the melting point of the UHMWPE filaments under the applied conditions, while keeping the cable (and thus its filaments) under elongational tension, for a certain time period, so that the filaments in the cable stick together at their surface enough to increase the stiffness of the cable, but in such a way that upon bending of the cable at least part of the filaments are separate to decrease the stiffness of the cable. The temperature range for the heat setting process preferably is between 140 and 151° C., more preferably between 145 and 149° C. Above 145° C. a fast and economic process for sticking the filaments together is possible. Below 149° C. there is no or only a limited chance that the filaments melt and fuse together, so that they don't separate again by bending the cable. The elongational tension applied may induce optimizing the structure of the cable by slightly rearranging the strands and filaments in the cable such that all are (more equally) tensioned, and resulting in some elongation of the cable. This better stress distribution results in higher strength efficiency; that is more filaments contribute to the strength of the cable. In addition, the elongational tension may, in combination with the elevated temperature, also result in some stretching or drawing of the UHMWPE filaments. It is known that post-stretching of filaments generally results in an improvement of their tensile strength.

Preferably, the cable was heat-set in a gaseous medium, for example in air or in a non-oxidative atmosphere like nitrogen gas. It was found that a cable that was heat-set in a gaseous rather than a liquid medium, for example superheated water, shows an increased stiffness that can be more effectively decreased again upon flexing the cable. A further advantage of heat-setting in a gaseous medium is that the heat-setting medium does not need to be removed from the cable in a subsequent step.

Suitable exposure times during the heat setting process are on the order of several minutes, e.g. from 2-10 minutes; a higher heat-setting temperature generally enabling shorter times of exposure. Preferably such elongational tension was applied, that the cable was stretched with a stretch ratio (ratio of cable length after and before heat-setting) of from 1.05 to about 3.0, more preferably of 1.1-2.5, or even 1.2-2.0. The advantage of a higher temperature is that bending stiffness increased more effectively, or in a shorter time. Applying a higher stretch ratio results in higher tenacity, but this effects appears to level off at stretch ratio above about 2. Bending stiffness of the cable also appears to level off for products stretched at a ratio of more than about 2 on an absolute scale (free length of cable that shows specific bending); but relative to its dimensions (titer) bending stiffness is found to increase with applied stretch ratio.

The elongate surgical repair product according to the invention comprises a heat-set cable having a bending stiffness that can be lowered, which means that its bending stiffness locally decreases upon bending the cable at least one time at an angle of at least 90° preferably at a radius below 5 mm, more preferably below 1 mm (lower stiffness specifically at the place of bending). Preferably the cable is bended up and down (flexed) several times. Bending the cable at a larger angle, e.g. up to 180°, is more effective in lowering the stiffness. After repeated bending, the flexural stiffness generally approaches the level of a cable (of similar construction and thickness or titer) that was not heat-set. The heat-set cable shows such flexural stiffness, that a certain minimum length of cable, without being supported, will not bend over under its own weight; which makes handling of the cable during surgical operation much easier and more controlled. Bending the cable, for example upon making a first knot for securing will already reduce stiffness, such that placing subsequent knots is facilitated.

The elongate surgical repair product according to the invention comprises a heat-set cable having a bending stiffness that can be lowered, with a ratio of initial bending stiffness to lowered bending stiffness in the range of about 2 to 15; wherein bending stiffness is determined as the length of cable freely protruding from a vertical tube until the cable end bends over to below the horizontal plane of the edge of the vertical tube. Preferably, said stiffness ratio is in the range 2-10, more preferably 3-10.

The invention further relates to a method of making an elongate surgical repair product according to the invention, comprising the steps of assembling a plurality of strands comprising HPPE yarn that substantially consists of a plurality of UHMWPE filaments and optionally strands comprising other fibrous materials to form a cable, and heat-setting the cable by subjecting it to a heat treatment at elevated temperature but below the melting point of the UHMWPE filaments under the applied conditions, while keeping the cable under elongational tension, preferably between 140 and 151° C., more preferably between 145 and 149° C.

Suitable methods for assembling a plurality of strands include twisting, knitting, weaving and braiding techniques. The number of strands in the member is not specifically limited, but the number of strands (or yarns) for making a member is 2, typically 3 or more. To make a heavier member, preferably a higher number of strands (or yarns) of certain titer is applied, rather than using the same number of strands but increasing their titer; the member thus made shows more decrease in stiffness upon bending.

Preferably, the assembling step in the method according to the invention concerns braiding the plurality of strands comprising HPPE yarns into a cable.

The step of heat-setting the cable is preferably performed in a gaseous medium, for example in air or in a non-oxidative atmosphere like nitrogen gas to result in a temporary increase in stiffness. It was found that performing the heat-treatment in a liquid medium, for example superheated water, results in an increased stiffness, which stiffness cannot as effectively be decreased again by simply bending the cable.

The elongational tension that is applied during the heat-setting process is preferably kept at a constant level, to make a product with consistent properties. The tension applied can be adjusted to result in a certain stretching of the cable. Care should be taken not to over-stretch the cable or its filaments, and to prevent breaking of the cable.

Preferred conditions for the heat-setting step in the method according to the invention, like temperature, time, applied elongational tension or stretching, and for structure and composition of strands, yarn and filaments are analogous to those discussed above.

The heat-setting can be performed in a single step, but also in multiple steps, for example with the temperature increasing with each step, or applying increasing elongational tension.

In the method according to the invention care should be taken to handle the cable after the step of heat-setting in such way that its bending stiffness is not prematurely reduced; that is, bending and flexing should be omitted where possible. The elongate surgical repair product is for example preferably packed in elongated state; or after winding in (parallel) loops of relatively large diameter.

The process according to the invention may further comprise one or more additional steps, including such steps as coating the cable, attaching a needle or bone anchor, packing, and sterilizing. Such steps are known to the skilled person.

The invention further relates to the use of a heat-set cable comprising at least 50 mass % of HPPE yarn that substantially consists of a plurality of ultra-high molar mass polyethylene filaments for making a surgical repair product. It is surprisingly found that such a cable shows a flexural stiffness that markedly reduces upon bending the cable; which makes it very suited for use as surgical suture or cable (stiffness to ease initial handling by a surgeon, flexibility to allow securing of the cable, and to prevent irritation of body tissue).

The invention further relates to a kit for a surgical method, comprising a sterile surgical repair product comprising a fibrous member of which bending stiffness can be lowered according to the invention. The kit may further comprise for example auxiliary surgical tools, and/or complementary instructions for use.

The invention further relates to a surgical method, comprising the steps of approximating at least two tissue or bone parts, or attaching tissue and implant parts, with an elongate surgical repair product comprising a fibrous member of which bending stiffness can be lowered according to the invention, and bending the member at least once to reduce its stiffness.

The invention will be further elucidated with reference to the following non-limiting examples.

Comparative Experiment A 8 strands of a HPPE multifilament yarn of 226 dtex, having a tenacity of 3.8 N/tex and tensile modulus of 130 N/tex, were braided on a Herzog braiding machine into a cable with about 5.9 picks per centimeter.

Braid properties were determined applying following methods:

Tensile properties: tensile strength (or tenacity), tensile modulus (or modulus) and elongation at break (or eab) are defined and determined with a procedure in accordance with ASTM D885M, using a nominal gauge length of the fibre of 500 mm, a crosshead speed of 50%/min, and Instron 2714 clamps, of type Fibre Grip D5618C for multifilament yarn. Strength of braided members was measured on a Zwick 1435 apparatus with Instron 1497K clamps. On the basis of the measured stress-strain curve the modulus is determined as the gradient between 0.3 and 1% strain. For calculation of the modulus and tenacity, the tensile forces measured are divided by the titer, as determined by weighing 10 meters of yarn or 1 meter of cable.

Bending stiffness of a cable was determined by slowly entering the cable into the lower opening of a vertically positioned tube of 150 mm length and suitable diameter (4 mm in this case) until the cable protruding from the top opening bended under its own weight and the cable end passed below the horizontal plane of the top opening of the tube (cable not being supported other than by the edge of the tube). Experiments were performed before and after flexing the cable over its length by moving it 10 times over a stainless steel bar of 1 mm diameter at an angle of 90°, while being tensioned with a mass of 1.5 kg. Stiffness is expressed as the length of cable extending from the tube (average of 5 experiments);

Stress relaxation was measured on a cable, by tensioning the cable in a tensile tester with 1 or 1.5 N/tex, and measuring the residual stress after 5 and 10 minutes; reported values are expressed as % of initial stress (average of 2 experiments).

EXAMPLES 1-3

A braided cable was made as in Comp. Exp. A, and subsequently heat-set by feeding it into one end of a hot air oven kept at a constant temperature of 140° C., with a feeding rate of 2 m/min (controlled by feeding rolls). The cable trajectory in the oven was 8.4 meter, and the winding speed after exiting the oven at the other end was varied to result in stretch ratios of 1.11, 1.28 and 1.43, respectively. Properties were determined as indicated above; results are collected in Table 1.

EXAMPLES 4-7

Examples 1-3 were repeated, with the oven temperature setting now being 151° C. Stretch ratios of 1.13, 1.34, 1.55, and 2.33 were applied, respectively. Results are also listed in Table 1.

It can be seen that bending stiffness increases with increasing heat-setting temperature and applied stretch ratio. The heat-set cable shows an initial stiffness, that can be about 2-5 fold lowered upon bending the cable several times, and is then at a level similar to a non heat-set cable (normalized to cable titer). The heat-set cable also shows a higher level of residual stress in relaxation tests.

The invention claimed is:

1. An elongate surgical repair product comprising a cable having an initial bending stiffness, wherein
the cable exhibits a subsequent bending stiffness which is lower than the initial bending stiffness, the lower subsequent bending stiffness being obtained solely in response to bending of the elongate surgical repair product having the initial bending stiffness without removing a component thereof, wherein
a ratio of the initial bending stiffness to the subsequent bending stiffness is in a range of about 3 to 10, and wherein
the cable comprises at least 50 mass % of high-performance polyethylene yarn consisting essentially of a plurality of ultra high molecular weight polyethylene (UHMWPE) filaments, the cable having been heat-set under elongational tension at a heat-setting temperature between 140 and 151° C. but below a melting point of the UHMWPE filaments for a time period of 2-10 minutes to cause surfaces of the filaments in the cable to stick together sufficiently to increase the bending stiffness of the cable following heat setting while yet allowing at least a part of the filaments of the cable to separate from one another in response to bending thereby lowering the bending stiffness of the cable at a place of the bending.

2. The surgical repair product according to claim 1, wherein the high-performance polyethylene yarn has a tenacity of at least 2.0 N/tex.

3. The surgical repair product according to claim 1, wherein the cable is of a braided construction.

4. The surgical repair product according to claim 1, wherein the fibrous member comprises strands, and wherein the strands comprise at least 60 mass % of high-performance polyethylene yarn.

5. The surgical repair product according to claim 1, wherein the cable has a linear density of about 20-3000 tex.

6. The surgical repair product according to claim 1, wherein the heat-setting temperature is between 145 and 149° C.

7. A method of making an elongate surgical repair product according to claim 1, comprising the steps of:
(a) assembling a plurality of strands comprising high-performance polyethylene yarn that substantially consists of a plurality of UHMWPE filaments and optionally strands comprising other fibrous materials to form a cable, and

TABLE 1

| Sample | Dimensions | | Tensile properties | | | Bending stiffness | | | | ratio (initial/ after) | Residual stress | | | |
| | | | | | | | | | | | At 1 N/tex; 5 min. | At 1 N/tex; 10 min. | At 1.5 N/tex; 5 min. | At 1.5 N/tex; 10 min. |
| | Titer (tex) | Diameter (mm) | Tenacity (N/tex) | Modulus (N/tex) | eab (%) | Initial (mm) | (mm/tex) | After bending (mm) | (mm/tex) | | (%) | (%) | (%) | (%) |
| Comp. exp. A | 186 | 0.5 | 2.8 | 30 | 4.4 | 98 | 0.5 | 98 | 0.5 | 1 | 67 | 61 | 70 | 66 |
| Ex. 1 | 168 | 0.46 | 3.4 | 111 | 3.3 | 252 | 1.5 | 63 | 0.4 | 3.5 | 77 | 73 | 79 | 75 |
| Ex. 2 | 145 | 0.39 | 3.5 | 130 | 3.0 | 252 | 1.7 | 77 | 0.5 | 3.0 | 80 | 77 | 80 | 77 |
| Ex. 3 | 130 | 0.27 | 3.3 | 134 | 2.9 | 244 | 1.9 | 71 | 0.5 | 3.4 | 78 | 74 | 79 | 76 |
| Ex. 4 | 165 | 0.38 | 2.8 | 31 | 3.4 | 282 | 1.7 | 71 | 0.4 | 4.3 | | | | |
| Ex. 5 | 139 | 0.36 | 3.3 | 121 | 3.0 | 300 | 2.2 | 89 | 0.6 | 3.7 | | | | |
| Ex. 6 | 120 | 0.30 | 3.4 | 138 | 2.8 | 278 | 2.3 | 71 | 0.6 | 3.8 | | | | |
| Ex. 7 | 80 | 0.18 | 3.5 | 168 | 2.5 | 208 | 2.6 | 83 | 1 | 2.6 | | | | |

(b) subjecting the cable to a heat-setting treatment at a temperature between 140 and 151° C. but below the melting point of the UHMWPE filaments while keeping the filaments of the cable under elongational tension for a time period of 2-10 minutes so that the filaments in the cable stick together at their surface sufficiently to increase the stiffness of the cable while yet permitting at least part of the filaments to separate upon bending of the cable to thereby decrease the stiffness of the cable at a place of the bending.

8. The method according to claim 7, wherein the heat-setting treatment is carried out at a temperature between 145 and 149° C.

9. The method according to claim 7, wherein step (a) comprises braiding the plurality of strands.

10. The method according to claim 7, wherein keeping the filaments of the cable under elongational tension is performed by stretching the cable with a stretch ratio of from 1.05 to 3.0.

11. The method according to claim 10, wherein the stretch ratio is from 1.2 to 2.0.

12. A kit for a surgical method, comprising a sterile surgical repair product comprising a cable according to claim 1.

* * * * *